(12) United States Patent
Parthasarathy et al.

(10) Patent No.: US 8,761,852 B2
(45) Date of Patent: *Jun. 24, 2014

(54) DISPOSABLE OXIMETER DEVICE

(75) Inventors: Jayant Parthasarathy, Eden Prairie, MN (US); Matthew Prior, Plymouth, MN (US)

(73) Assignee: Nonin Medical, Inc., Plymouth, MN (US)

(*) Notice: Subject to any disclaimer, the term of this patent is extended or adjusted under 35 U.S.C. 154(b) by 893 days.

This patent is subject to a terminal disclaimer.

(21) Appl. No.: 12/707,467

(22) Filed: Feb. 17, 2010

(65) Prior Publication Data

US 2010/0210924 A1    Aug. 19, 2010

Related U.S. Application Data

(60) Provisional application No. 61/153,566, filed on Feb. 18, 2009.

(51) Int. Cl.
*A61B 5/1455* (2006.01)

(52) U.S. Cl.
USPC .......................... 600/323; 600/310; 600/322

(58) Field of Classification Search
USPC .................................. 600/309–344
See application file for complete search history.

(56) References Cited

U.S. PATENT DOCUMENTS

| | | | |
|---|---|---|---|
| 4,865,038 A * | 9/1989 | Rich et al. | 600/344 |
| 5,209,230 A | 5/1993 | Swedlow et al. | |
| 5,237,994 A | 8/1993 | Goldberger | |
| 5,337,744 A | 8/1994 | Branigan | |
| 5,452,717 A | 9/1995 | Branigan et al. | |
| 6,149,481 A | 11/2000 | Wang et al. | |
| 6,546,267 B1 | 4/2003 | Sugiura et al. | |
| 6,622,034 B1 | 9/2003 | Gorski et al. | |
| 6,745,061 B1 | 6/2004 | Hicks et al. | |
| 6,763,256 B2 | 7/2004 | Kimball et al. | |
| 2003/0171662 A1 | 9/2003 | O'Connor et al. | |

(Continued)

FOREIGN PATENT DOCUMENTS

| | | |
|---|---|---|
| JP | 2004049579 A1 | 2/2004 |
| JP | 2005110816 A1 | 4/2005 |

(Continued)

OTHER PUBLICATIONS

"International Application Serial No. PCT/US08/55155, International Search Report and Written opinion mailed Aug. 26, 2008", 15 pgs.

(Continued)

*Primary Examiner* — Eric Winakur
*Assistant Examiner* — Marjan Fardanesh
(74) *Attorney, Agent, or Firm* — Schwegman, Lundberg & Woessner, P.A.

(57) ABSTRACT

A device includes a pliable membrane, a sensor module and a communication module. The pliable membrane includes a semi-rigid structural member. The membrane is configured to conform to a tissue surface. The structural member is configured to retain the membrane in a particular shape corresponding to the tissue surface. The sensor module is coupled to the membrane. The sensor module is configured to generate an electrical signal corresponding to a physiological parameter associated with the tissue surface. The communication module is coupled to the membrane. The communication module is configured to receive the electrical signal and wirelessly communicate data corresponding to the electrical signal with a remote device.

23 Claims, 4 Drawing Sheets

(56) References Cited

U.S. PATENT DOCUMENTS

| | | |
|---|---|---|
| 2003/0181799 A1 | 9/2003 | Lindekugel et al. |
| 2004/0087845 A1 | 5/2004 | Katarow et al. |
| 2004/0116787 A1 | 6/2004 | Schnall |
| 2006/0106294 A1 | 5/2006 | Maser et al. |
| 2006/0173247 A1 | 8/2006 | Medina |
| 2007/0032710 A1 | 2/2007 | Raridan et al. |
| 2007/0078317 A1 | 4/2007 | Matlock |
| 2007/0123756 A1 | 5/2007 | Kitajima et al. |
| 2008/0208023 A1 | 8/2008 | Gruvac et al. |
| 2013/0310667 A1 | 11/2013 | Grubac et al. |

FOREIGN PATENT DOCUMENTS

| | | |
|---|---|---|
| JP | 2010519008 A | 6/2010 |
| WO | WO-2008106528 A2 | 9/2008 |
| WO | WO-2008106528 A3 | 9/2008 |
| WO | WO-2010096475 A1 | 8/2010 |

OTHER PUBLICATIONS

"International Application Serial No. PCT/US2008/055155, International Preliminary Examination Report mailed Sep. 11, 2009", 12 pgs.

"International Application Serial No. PCT/US2010/024464, Search Report mailed May 27, 2010", 6 pgs.

"International Application Serial No. PCT/US2010/024464, Written Opinion mailed May 27, 2010", 5 pgs.

"U.S. Appl. No. 11/679,595, Final Office Action mailed Mar. 15, 2012", 23 pgs.

"U.S. Appl. No. 11/679,595, Non Final Office Action mailed Jul. 11, 2011", 37 pgs.

"U.S. Appl. No. 11/679,595, Response filed Jul. 16, 2012 to Final Office Action mailed Mar. 15, 2012", 9 pgs.

"U.S. Appl. No. 11/679,595, Response filed Jul. 16, 2012 to Final Office Action mailed Mar. 15, 2012", 10 pgs.

"European Application Serial No. 10708441.0, Office Action mailed Dec. 5, 2011", 2 pgs.

"European Application Serial No. 10708441.0, Response filed Jun. 13, 2012 to Office Action mailed Dec. 5, 2011", 9 pgs.

"International Application Serial No. PCT/US2010/024464, International Preliminary Report on Patentability mailed Sep. 1, 2011", 7 pgs.

"Japanese Application Serial No. 2009-551826, Voluntary Amendment filed Feb. 25, 2011", 15 pgs.

"Japanese Application Serial No. 2009-551826, Office Action mailed May 21, 2013", with English translation of claims, 8 pgs.

European Application Serial No. 08730860.7, Extended European Search Report mailed Nov. 6, 2013, 10 pgs.

European Application Serial No. 10708441.0, Examination Notification Art. 94(3) mailed Nov. 28, 2013, 4 pgs.

* cited by examiner

DISPOSABLE OXIMETER DEVICE

CLAIM OF PRIORITY

This patent application claims the benefit of priority, under 35 U.S.C. Section 119(e), to U.S. Provisional Patent Application Ser. No. 61/153,566, entitled "DISPOSABLE OXIMETER DEVICE," filed on Feb. 18, 2009, and is incorporated by reference herein.

CROSS-REFERENCE TO RELATED PATENT DOCUMENTS

This document is related to U.S. application Ser. No. 11/679,595, FOLDABLE SENSOR DEVICE AND METHOD OF USING SAME, assignee Nonin Medical, Inc., filed Feb. 27, 2007, and is incorporated by reference herein.

BACKGROUND

Physiological data, including for example, oximetry data, can be useful for monitoring the health of a patient or the health of a particular organ.

Currently available technology for acquiring oximetry data, however, is limited in many ways and is inadequate to satisfy the demand for cost-effective health care.

OVERVIEW

An example of the present subject matter includes an inexpensive wireless apparatus that can be fitted to a patient and discarded after use. The apparatus can include a wireless communication module that allows communication with a remote device. The remote device can include a monitor, a display, a storage device, or other module. The apparatus can include an oximeter measuring device having a sensor module that generates data corresponding to pulse oximetry or regional oximetry. The apparatus includes a flexible structure that can be conformed to provide a close fit on a patient and wirelessly provide medical data to a remote device. After collecting oximeter data or other data while fitted to a patient, the apparatus can be discarded.

One example of the apparatus includes an oximeter module having hardware and software, a sensing element, a power management unit, a power supply, a power control module, and a communication module.

The sensing element can include one or more optical emitters and one or more optical detectors. The optical emitters and optical detectors are held in position by a carrier structure at a spacing that provides light energy to the tissue with a specific alignment. The light can be transmitted through the tissue or directed to reflect from the tissue. For example, one embodiment includes light directed to pass from a first side of the tissue to a second side of a tissue. Modulation of the detected light by traversing the optical path can provide oximetry data.

In addition, a sensing element can include a temperature sensor, a pulse sensor, a heart rate variability sensor, a cardiac output sensor, a respiration rate sensor, an accelerometer, a pressure sensor, a blood pressure sensor, an electrocardiography sensor, an electroencephalogram sensor, an electromyography sensor, an electrooculogram sensor, a heart rate variability sensor, an acoustic respiratory monitoring sensor, a pulse transit timing sensor, or other physiological parameter sensor.

The power management unit can be configured to detect the presence or absence of subject tissue. Electrical power for selected elements of the oximeter device can be controlled based on the output of the power management unit. For example, one embodiment includes a circuit to withhold electrical power to the sensing element and to the communication module in the absence of the subject tissue. The power management unit can include a mechanical presence detector (such as a switch) or a non-mechanical presence detector. A non-mechanical presence detector can include, by way of examples, an optical element or a capacitance or conductance-based detector.

The power supply can include a battery or other power storage device. For example, a low cost disposable battery can be used.

The power control module can include an electrical switch to control delivery of electrical power between the power supply and other elements of the apparatus. The power control module can include, for example, a plastic pull-tab that, when removed by a user, closes an electrical circuit to power the apparatus. In another example, the power control module can include a user-operable button or other type of switch.

The communication module can include a wireless communication transceiver configured to allow exchange of analog or digital data. By way of examples, the communication module can include a BLUETOOTH module, an infrared module, or other wireless transceiver. In one example, the communication module includes a radio frequency (RF) transceiver.

Example 1 includes a device comprising a pliable membrane, a sensor module, a communication module. The pliable membrane has a semi-rigid structural member and the membrane is configured to conform to a tissue surface and the structural member is configured to retain the membrane in a particular shape corresponding to the tissue surface. The sensor module is coupled to the membrane and is configured to generate an electrical signal corresponding to a physiological parameter associated with the tissue surface. The communication module is coupled to the membrane and the communication module is configured to receive the electrical signal and wirelessly communicate data corresponding to the electrical signal with a remote device.

Example 2 includes the sensor module of the device of example 1 and optionally includes at least one of a pulse oximetry sensor, a regional oximetry sensor, photoplethysmography sensor, a temperature sensor, a pressure sensor, an accelerometer, a pulse rate sensor, a cardiac output sensor, a blood pressure sensor, an electrocardiography sensor, an electroencephalogram sensor, an electromyography sensor, an electrooculogram sensor, a heart rate variability sensor, an acoustic respiratory monitoring sensor, or a pulse transit timing sensor.

Example 3 includes the device of any of examples 1 or 2 wherein the sensor module is affixed to a first portion of the membrane and the communication module is affixed to a second portion of the membrane. The sensor module is coupled to the communication module by an electrical conductor.

Example 4 includes the device of any of examples 1 to 3 and further includes a processor module coupled to the membrane. The processor module is configured to receive the electrical signal, execute an algorithm and generate a measure of the physiological parameter. The data includes the measure of the physiological parameter.

Example 5 includes the device of any of examples 1 to 4 wherein the membrane is configured to be continuously affixed to the tissue surface for a duration exceeding a day.

Example 6 includes the device of any of examples 1 to 5 wherein the structural member includes a malleable material.

Example 7 includes the device of any of examples 1 to 6 wherein the membrane includes at least one strain relief feature.

Example 8 includes the device of any of examples 1 to 7 wherein the membrane includes a hook and loop fastener.

Example 9 includes the device of any of examples 1 to 8 wherein at least one of the sensor module or the communication module is electrically shielded.

Example 10 includes a system comprising a wearable device and a remote device. The wearable device includes a conformable membrane. The membrane is reinforced by a semi-rigid support structure. The support structure is configured to retain the membrane in a shape that conforms to a tissue surface. The wearable device includes a sensor module and a first communication module. The sensor module is configured to generate an electrical signal based on a physiological parameter. The first communication module is configured to wirelessly communicate data based on the electrical signal. The remote device includes a second communication module. The second communication module is configured to wirelessly communicate the data. The remote device is configured to store information based on the physiological parameter.

Example 11 includes the system of example 10 wherein the sensor module includes at least one of a pulse oximetry sensor, a regional oximetry sensor, photoplethysmography sensor, a temperature sensor, a pressure sensor, an accelerometer, a pulse rate sensor, a cardiac output sensor, blood pressure sensor, an electrocardiography sensor, an electroencephalogram sensor, an electromyography sensor, an electrooculogram sensor, a heart rate variability sensor, an acoustic respiratory monitoring sensor, or a pulse transit timing sensor.

Example 12 includes the system of any of examples 10 or 11 wherein the wearable device includes a display.

Example 13 includes the system of any of examples 10 to 12 wherein the remote device includes at least one of a display, a user interface, a memory, a processor, or a network interface.

Example 14 includes the system of any of examples 10 to 13 wherein the sensor module is coupled to the first communication module by an electrical conductor.

Example 15 includes the system of any of examples 10 to 14 wherein the membrane includes a laminated assembly.

Example 16 includes the system of any of examples 10 to 15 wherein the membrane includes an aperture.

Example 17 includes the system of any of examples 10 to 16 wherein the aperture is configured to provide ventilation to an underlying tissue.

Example 18 includes the system of any of examples 10 to 17 wherein the membrane is configured for single patient use.

Example 19 includes the system of any of examples 10 to 18 wherein the membrane is configured to at least partially encircle a tissue.

Example 20 includes a method comprising providing a wearable device and configuring a remote device. The wearable device includes a pliable membrane having a structural member. The structural member is configured to retain the pliable membrane in a shape that conforms to a tissue surface. The device includes a sensor module and a communication module. The sensor module is configured to generate an electrical signal based on a physiological parameter corresponding to the tissue surface. The communication module is configured to wirelessly communicate data based on the electrical signal. The remote device is configured to receive the data and to store the data.

Example 21 includes the method of example 20 wherein configuring the remote device includes configuring a wireless radio frequency transceiver.

Example 22 includes the method of any examples 20 or 21 further including affixing the wearable device to a user.

Example 23 includes the method of any of examples 20 to 22 further including using the remote device to display the data.

These examples can be combined in any permutation or combination. This overview is intended to provide an overview of subject matter of the present patent application. It is not intended to provide an exclusive or exhaustive explanation of the invention. The detailed description is included to provide further information about the present patent application.

BRIEF DESCRIPTION OF THE DRAWINGS

In the drawings, which are not necessarily drawn to scale, like numerals may describe similar components in different views. Like numerals having different letter suffixes may represent different instances of similar components. The drawings illustrate generally, by way of example, but not by way of limitation, various embodiments discussed in the present document.

DETAILED DESCRIPTION

Figure 1:
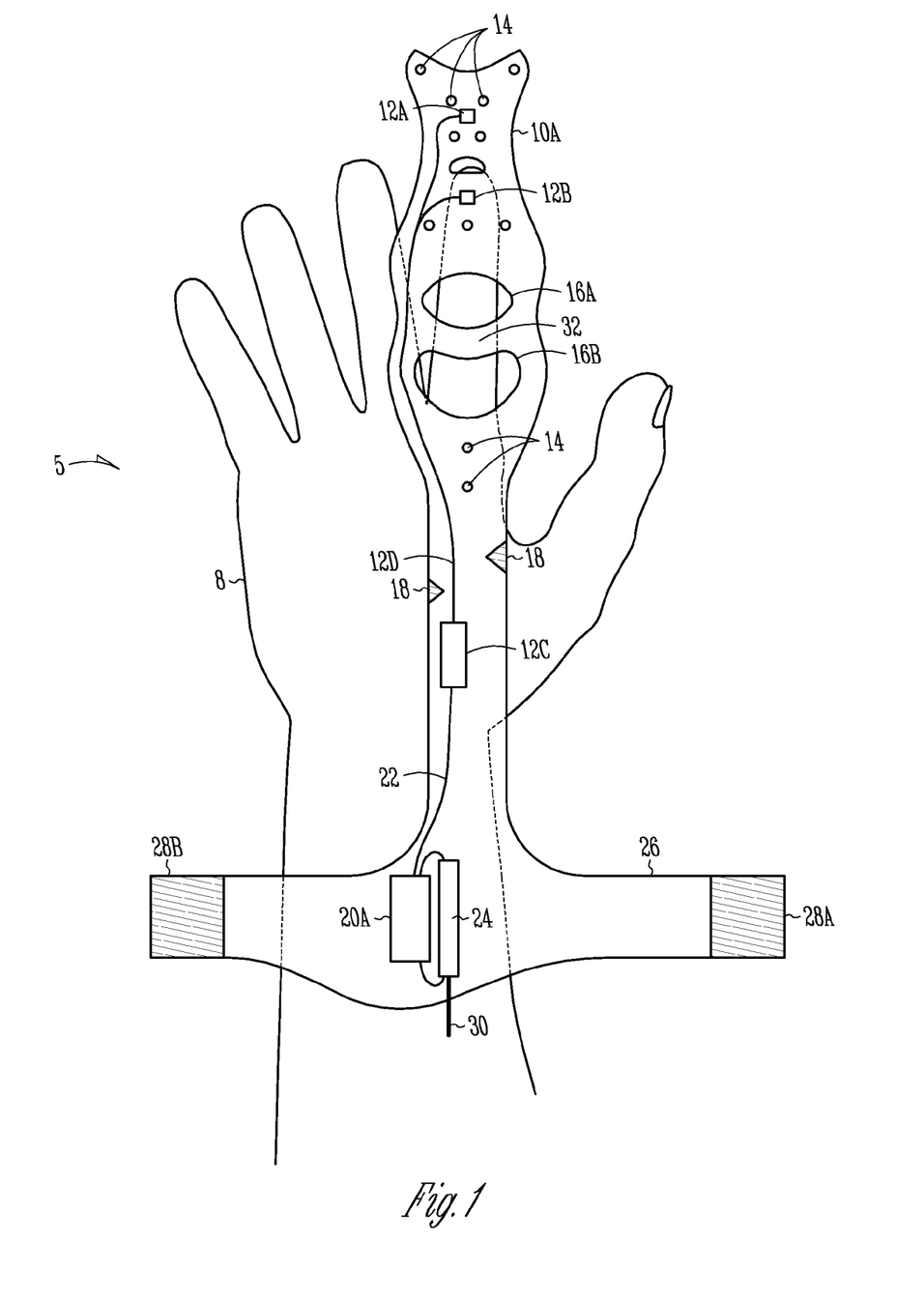
FIG. 1 includes a view of an apparatus, according to one example.

FIG. 1 illustrates system 5 including device 10A in an un-folded configuration. The apparatus includes a structure that can be deformed to accommodate a hand shape, for example. One example includes a pliable membrane including a plurality of foam (polyurethane) layers in a laminated arrangement. A layer in contact with the tissue can be open-cell foam (for patient comfort) and an outer layer can include a closed-cell foam (for ease of cleaning).

Device 10A, in the example illustrated, includes a plurality of apertures including ventilation holes 14. Ventilation holes 14 are sized and distributed to provide circulation to the underlying tissue site, provide breathability, and prevent overheating of the user. In addition, apertures 16A and 16B are sized and distributed to provide clearance for a finger or other tissue. In the example shown, aperture 16A and aperture 16B are separated by bridge 32.

Device 10A includes a sensor module, here depicted to include distributed components including sensor element 12A, sensor element 12B, and sensor element 12C. In other examples, the sensor module is a unitary component that includes a sensor and associated circuitry in a single package. In the example shown, sensor element 12A includes an optical emitter and sensor element 12B includes an optical detector. Sensor element 12A and sensor element 12B are configured to provide light at a particular wavelength and detect light in order to generate a signal suitable for photoplethysmography. For example, the sensor module can generate a signal corresponding to pulse oximetry or tissue oximetry (regional oximetry). Sensor element 12A, sensor element 12B and sensor element 12C are coupled, in the example shown, by electrical conductor 12D.

Device 10A also includes communication module 20A. Communication module 20A is coupled to sensor module by electrical conductor 22. Electrical conductor 22 (as well as conductor 12D) can include a flexible conductor, such as braided wire, litz wire, or other multi-strand wire.

Communication module 20A can include, in various example, a transmitter, a receiver, or a transceiver. Communication module 20A can include a radio frequency (RF) circuit, an infrared (IR) device, an ultrasonic device, or other wireless communication module. In one example, communication module 20A includes a BLUETOOTH transceiver or other such device configured for ad hoc wireless communication using a peer-to-peer or other networking configuration.

In the example shown, communication module 20A and the sensor module are powered by power supply 24. Power supply 24 can include a battery, a fuel cell, an energy storage device, or other portable power source. Power supply 24 is controlled by switch 30. Switch 30 can include a manually operable switch such as a removable tab that connects the power supply to a circuit of device 10A. In one example, switch 30 includes a physically releasable contact.

In one example, power supply 24 is controlled by a power management module. The power management module can be included in communication module 20A, power supply 24, or other circuitry of device 10A.

In one example, the power management module is configured to detect the presence or absence of a user. For example, a mechanical switch, a capacitance-based detector, a resistance-based detector, or other type of device can be configured to sense the presence of device 10A affixed to a user, and deliver current from power supply 24 as appropriate.

Device 10A can include a processor module disposed in any of the sensor module, the communication module, or other component. The processor module can be configured to receive an output from the sensor module, execute an algorithm using a processor and a set of instructions to determine information regarding the physiological parameter and provide the information to the communication module for forwarding to the remote device.

In one example, the remote device provides instructions for execution by the wearable device. In such an example, the processor module executes instructions to implement the changes or perform analysis or calibration as requested by the remote device. In one example, the wearable device includes memory for storage of instructions and data for use by the wearable device.

In one example, one or more of the electrical components (such as the sensor module, the communication module, a power management module, a processor module) is electrically shielded. Electrical shielding can isolate the various components and provide patient protection. Shielding can include measures to prevent or reduce electrostatic shock, reduce stray currents, and provide electrical isolation with respect to the tissue.

Device 10A also includes strap 26. Strap 26 is configured to at least partially encircle a portion of a user, such as a wrist, ankle, or other tissue. Strap 26 includes a fastener mechanism, shown here as distributed as fastener portion 28A and fastener portion 28B. Fastener portion 28A and fastener portion 28B can include, for example, a buckle, or a hook and loop type fastener (sometimes referred to as Velcro).

Device 10A includes relief features 18. Relief features 18 are depicted as triangular shaped cuts; however a lateral slit or other configuration can also be used. Relief features 18 allow the finger portion of device 10A to flex in a side to side direction with movement of the finger relative to the wrist portion. In addition, relief features 18 allow repositioning of the finger portion of device 10A without disturbing strap 26. In the figure, the sensor module is aligned to detect a physiological parameter associated with the index finger. In addition, relief features 18 allow the finger portion to be repositioned to align with any other finger, such as the ring finger.

Figure 2:
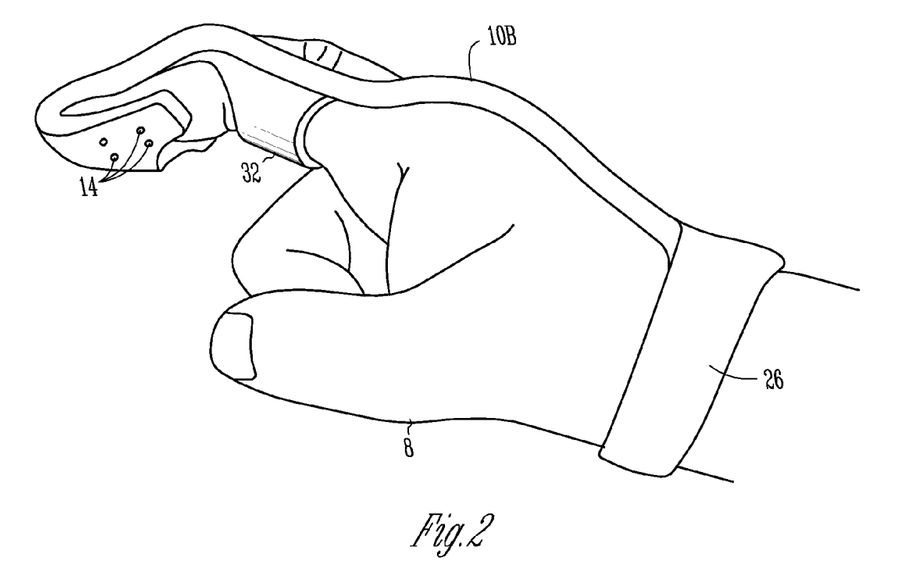
FIG. 2 includes a view of an apparatus positioned on a finger, according to one example.

FIG. 2 illustrates a view of hand 8 with device 10B in position on the index finger. Ventilation holes 14 are visible in the finger portion. In addition, bridge 32 is illustrated below a portion of the finger. Strap 26 is shown encircling the user's wrist.

Figure 3:
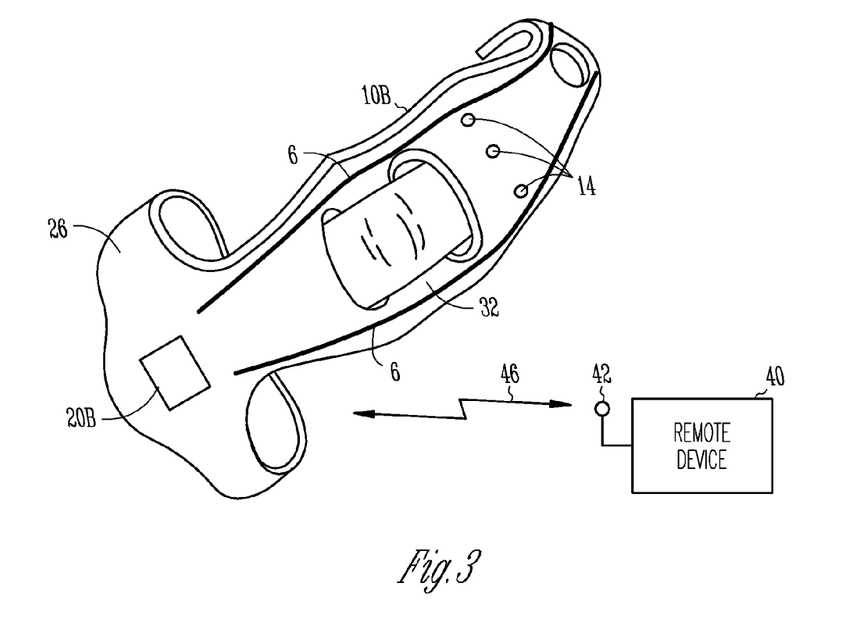
FIG. 3 includes a view of an apparatus in communication with a remote device, according to one example.

FIG. 3 illustrates device 10B in communication with remote device 40. In this view, a portion of the finger is visible atop bridge 32. Ventilation holes 14 provide cooling. The wrist (not shown) is encircled by strap 26.

Device 10B includes semi-rigid structural member 6. Structural member 6 can include a malleable wire that is embedded in or affixed to the pliable membrane of device 10B. In this example, structural member 6 can include two separate wire elements or a contiguous wire element with a bight at the fingertip region (not visible in this view).

Communication module 20B is affixed to a surface of device 10B and in this example, includes a wireless communication module such as an RF transceiver. As denoted by communication link 46, communication module 20B enables wireless communication between device 10B and remote device 40 (via antenna 42). Antenna 42 can include a radio frequency (RF) antenna. In one example, remote device 40 and device 10B communicate wirelessly using an infrared link.

Remote device 40 can be configured to exchange information corresponding to tissue oximetry, pulse oximetry, or other physiological parameter. Remote device 40 can include a memory or other data storage device as well as a processor. In addition, remote device 40 can include various types of software, firmware or hardware including, for example, a printer, a display, a network interface, or a user interface.

Figure 4A:
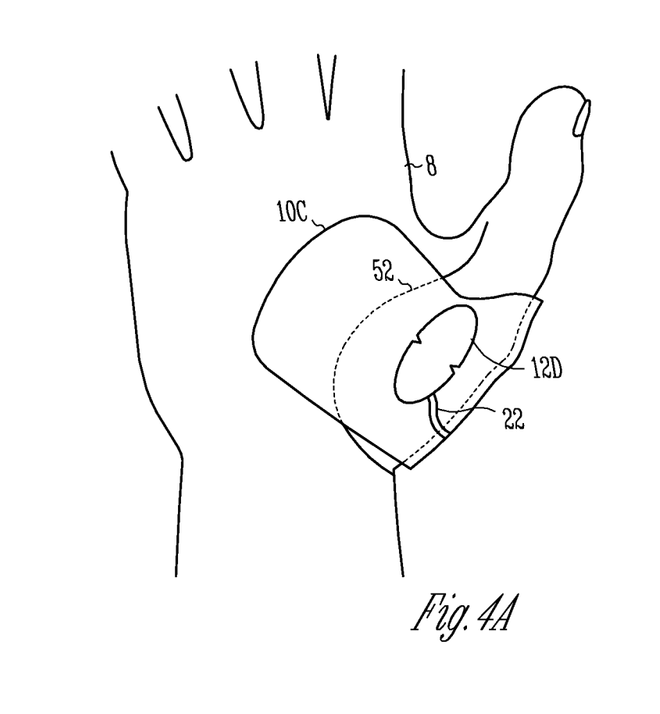
FIGS. 4A, 4B, and 4C illustrate views of an apparatus configured for use on a thenar eminence, according to one example.
Figure 4B:
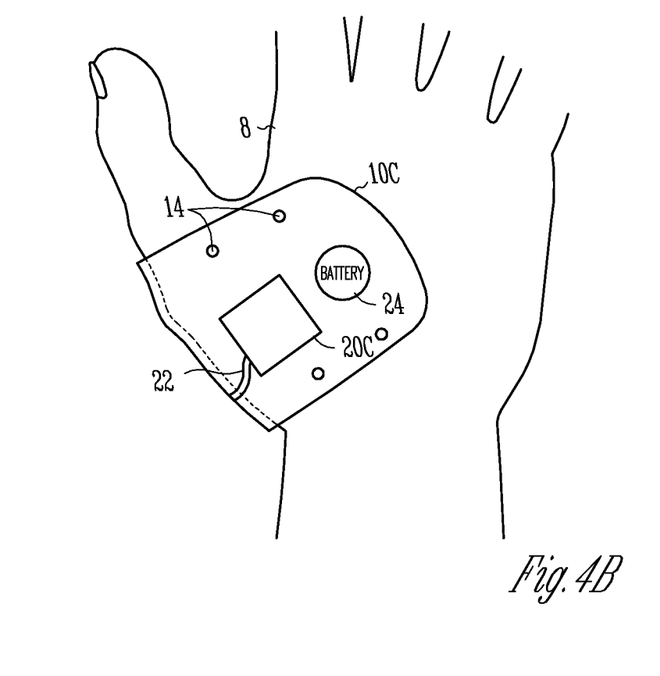
Figure 4C:
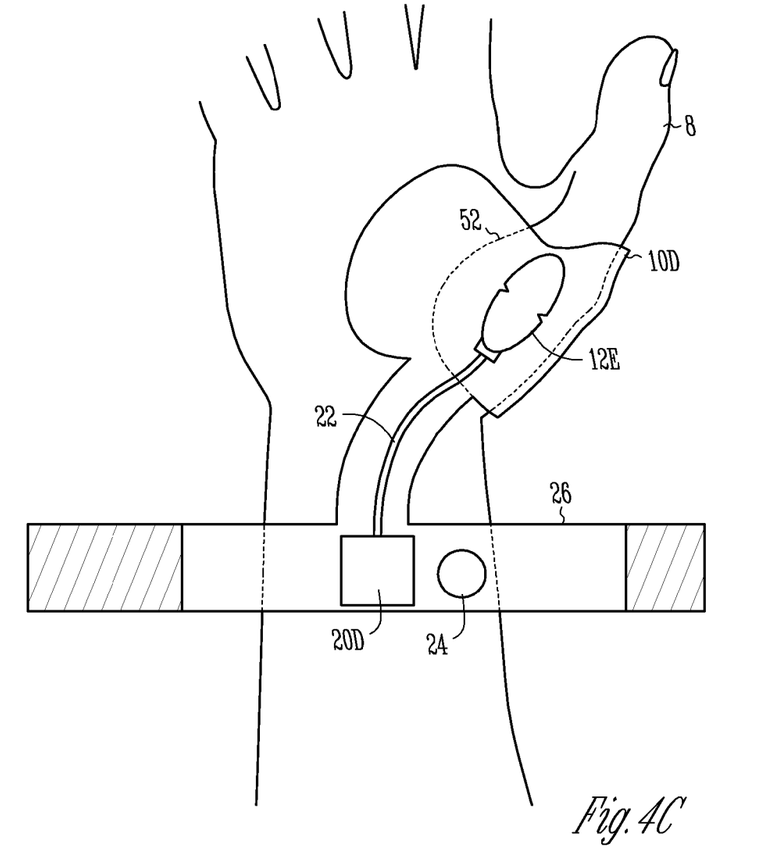

FIGS. 4A, 4B, and 4C illustrate a durable, disposable wireless device suitable for use in monitoring a physiological parameter associated with the thenar eminence. In FIG. 4A, hand 8 is shown with palm-up and is partially encircled (or wrapped) by conformable device 10C. Device 10C is configured to position sensor module 12D atop thenar eminence (bounded by line 52). Sensor module 12D is coupled by electrical conductor 22 to a module on an opposite side of the hand.

In FIG. 4B, hand 8 is shown with palm-down and electrical conductor 22 is coupled to communication module 20C. Communication module 20C and power supply 24 are visible on this side of the device 10C. Ventilation holes 14 are also visible in the portion shown in FIG. 4B. In one example, device 10C is held in place by the contours of the tissue surface formed by the thenar eminence. In one example, an adhesive is used to bond hand 8 and device 10C.

FIG. 4C includes an illustration in which device 10D includes sensor module 12E. Sensor module 12E is electrically coupled, via conductor 22, to communication module 20D. Communication module 20D and power supply 24 are located on strap 26. Strap 26 is configured to encircle a wrist of a user.

Figure 5:
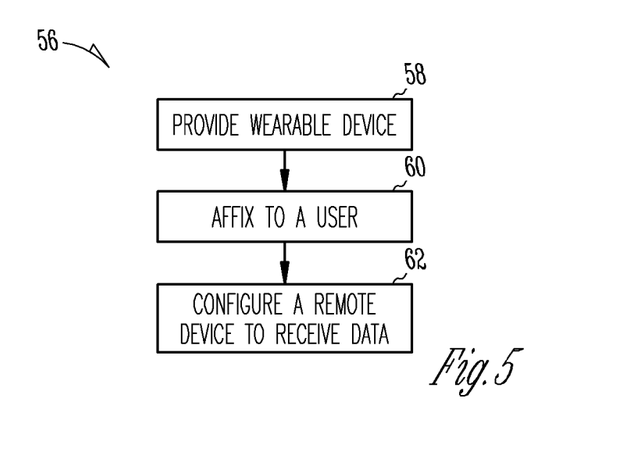
FIG. 5 includes a flow chart of a method, according to one example.

FIG. 5 illustrates method 56 according to one example. Method 56 includes, at 58, providing a wearable device. The wearable device includes a pliable membrane having a semi-rigid structural member. The pliable membrane can be configured to conform to a tissue surface. The semi-rigid structural member can include a malleable wire that maintains the shape of the pliable membrane. The wearable device includes a sensor module and a wireless communication module. At 60, the device is affixed to a user. The device can be affixed by manipulating the pliable membrane (along with the semi-rigid structural member) to conform to the tissue surface.

At 62, method 56 includes configuring a remote device to receive data from the wearable device. The data can be received and stored, or printed, or processed, or displayed or forwarded using a network interface.

Additional configurations or variations are also contemplated. For example, the sensor module (or the communication module) can be affixed to a surface of the pliable membrane or embedded within a layer (or between layers) of the membrane.

The device can be configured for disposal. For example, a low cost transceiver and sensor can be used with a foam-based pliable membrane. As such, the device can be configured for single patient use. The device can be used on a single patient and discarded thereafter. In one example, the device can be configured for continuous use of several days. For example, the foam laminate of the pliable membrane can have a surface suitable for direct contact with the patient tissue and a surface suitable for moisture release. The device can be configured for comfortable wear on a single patient for several days. In one example, the device can be repositioned to align the sensor module with a different finger or a different toe and is suitable for approximately 4-days use.

In one example, the sensor module and the communication module are housed within a single package. In addition, the package can include hardware, firmware, software and sensing elements, as well as power management unit, a battery, a power-on mechanism, as well as a wireless transceiver.

The device can be configured to acquire data continuously, periodically, or intermittently. For example, one configuration provides that upon actuation (of switch 30), the device continuously records and transmits data corresponding to a physiological parameter. In one example, the data is stored within the device and forwarded according to a schedule, or upon request, or upon detection of a particular event.

In one example, the pliable membrane (along with the semi-rigid structural member) provides protection for the electronic circuitry (including the sensor elements, the communication module, power management module, and the battery).

The pliable membrane can be deformed to conform to the shape and contour of a finger, a toe of a patient or other user. The pliable membrane can include a malleable structure configured to maintain a particular shape. The structure can include a semi-rigid component including, for example, a soft wire or metal spine to maintain the formed shape. For example, a perimeter wire embedded in the laminations or affixed to a surface of the foam can be used to retain a particular shape.

A wrist portion is provided to encircle the patient's wrist and to stabilize the apparatus when installed. The wrist portion can also be used to encircle an ankle or other body portion of the patient. The wrist portion can include a hook-and-loop type closure, an adhesive region, or other attachment mechanism.

A power supply is located near the wrist portion in the example shown. The power supply can include a battery. In the example shown, the power supply includes a pull tab that actuates an electrical switch to energize the apparatus with electrical power.

The example shown also includes a circuit module located near the power supply.

An electrical conductor carries current between the various modules.

Strain relief elements are provided along the length of the base structure. In the example shown, the strain relief elements include v-shaped notches along edges of the foam laminate. The notches allow the finger portion of the base structure to be affixed to any of the fingers while the wrist portion encircles the patient wrist.

Various types of strain relief elements are contemplated. In addition to v-shaped notches, the strain relief can include one or more transverse slits along the edges of the foam laminate. In one example, the strain relief elements are omitted and the length portion of the base structure is twisted by approximately 90 degrees to accommodate different fingers for the finger portion. The strain relief can accommodate re-positioning of the finger portion of the apparatus to mitigate tissue degradation (damage) at a sensor site.

According to one example, a pair of finger apertures is provided at the finger portion of the pliable membrane. The finger apertures are separated by a bridge portion of the base structure. When positioned on a patient, the bridge portion can be configured to pass beneath the finger and the finger can be passed through the finger apertures.

A plurality of vents is provided in selected locations of the pliant membrane. The vents enable the tissue to breathe and dissipate heat or moisture.

In one example, the finger portion includes sense elements. The sense elements can include any number or combination of an optical emitter, an optical detector, a temperature sensor, a pressure sensor, an accelerometer, or other sensor tailored to provide data concerning a physiological parameter.

A fold relief opening in the finger portion can be aligned with an end of the finger and ease formation of the fitted apparatus about the patient.

The pliant membrane maintains the sense elements in a relatively fixed alignment and position with respect to the tissue and other elements of the system. In one example, the sense elements include any combination of transmission or reflectance-based sensors that can provide regional oximetry data.

Additional Notes

The above detailed description includes references to the accompanying drawings, which form a part of the detailed description. The drawings show, by way of illustration, specific embodiments in which the invention can be practiced. These embodiments are also referred to herein as "examples." Such examples can include elements in addition to those shown or described. However, the present inventors also contemplate examples in which only those elements shown or described are provided. Moreover, the present inventors also contemplate examples using any combination or permutation of those elements shown or described (or one or more aspects thereof), either with respect to a particular example (or one or more aspects thereof), or with respect to other examples (or one or more aspects thereof) shown or described herein.

All publications, patents, and patent documents referred to in this document are incorporated by reference herein in their entirety, as though individually incorporated by reference. In the event of inconsistent usages between this document and those documents so incorporated by reference, the usage in the incorporated reference(s) should be considered supplementary to that of this document; for irreconcilable inconsistencies, the usage in this document controls.

In this document, the terms "a" or "an" are used, as is common in patent documents, to include one or more than one, independent of any other instances or usages of "at least one" or "one or more." In this document, the term "or" is used to refer to a nonexclusive or, such that "A or B" includes "A but not B," "B but not A," and "A and B," unless otherwise indicated. In the appended claims, the terms "including" and "in which" are used as the plain-English equivalents of the respective terms "comprising" and "wherein." Also, in the following claims, the terms "including" and "comprising" are open-ended, that is, a system, device, article, or process that includes elements in addition to those listed after such a term in a claim are still deemed to fall within the scope of that claim. Moreover, in the following claims, the terms "first," "second," and "third," etc. are used merely as labels, and are not intended to impose numerical requirements on their objects.

Method examples described herein can be machine or computer-implemented at least in part. Some examples can include a computer-readable medium or machine-readable medium encoded with instructions operable to configure an electronic device to perform methods as described in the above examples. An implementation of such methods can include code, such as microcode, assembly language code, a higher-level language code, or the like. Such code can include computer readable instructions for performing various methods. The code may form portions of computer program products. Further, the code may be tangibly stored on one or more volatile or non-volatile tangible computer-readable media during execution or at other times. These computer-readable media may include, but are not limited to, hard disks, removable magnetic disks, removable optical disks (e.g., compact disks and digital video disks), magnetic cassettes, memory cards or sticks, random access memories (RAMs), read only memories (ROMs), and the like.

The above description is intended to be illustrative, and not restrictive. For example, the above-described examples (or one or more aspects thereof) may be used in combination with each other. Other embodiments can be used, such as by one of ordinary skill in the art upon reviewing the above description. The Abstract is provided to comply with 37 C.F.R. §1.72(b), to allow the reader to quickly ascertain the nature of the technical disclosure. It is submitted with the understanding that it will not be used to interpret or limit the scope or meaning of the claims. Also, in the above Detailed Description, various features may be grouped together to streamline the disclosure. This should not be interpreted as intending that an unclaimed disclosed feature is essential to any claim. Rather, inventive subject matter may lie in less than all features of a particular disclosed embodiment. Thus, the following claims are hereby incorporated into the Detailed Description, with each claim standing on its own as a separate embodiment. The scope of the invention should be determined with reference to the appended claims, along with the full scope of equivalents to which such claims are entitled.

What is claimed:

1. A device comprising:
   a pliable membrane having a semi-rigid structural member, the membrane configured to conform to a tissue surface and the structural member configured to retain a first portion of the membrane in a particular shape corresponding to the tissue surface and the membrane having an elongate second portion, the second portion connected to the first portion having a relief feature configured to allow flexure in a side to side direction, and the membrane including a third portion connected to the second portion, wherein the third portion includes a strap configured to at least encircle a user;
   a sensor module coupled to the membrane, the sensor module configured to generate an electrical signal corresponding to a physiological parameter associated with the tissue surface;
   a communication module coupled to the membrane, the communication module configured to receive the electrical signal and wirelessly communicate data corresponding to the electrical signal with a remote device.

2. The device of claim 1 wherein the sensor module includes at least one of a pulse oximetry sensor, a regional oximetry sensor, photoplethysmography sensor, a temperature sensor, a pressure sensor, an accelerometer, a pulse rate sensor, or a cardiac output sensor, blood pressure sensor, an electrocardiography sensor, an electroencephalogram sensor, an electromyography sensor, an electrooculogram sensor, a heart rate variability sensor, an acoustic respiratory monitoring sensor, or a pulse transit timing sensor.

3. The device of claim 1 wherein the sensor module is affixed to a first portion of the membrane and the communication module is affixed to a second portion of the membrane, the sensor module coupled to the communication module by an electrical conductor.

4. The device of claim 1 further including a processor module coupled to the membrane, the processor module configured to receive the electrical signal, execute an algorithm and generate a measure of the physiological parameter, and wherein the data includes the measure of the physiological parameter.

5. The device of claim 1 wherein the membrane is configured to be continuously affixed to the tissue surface for a duration exceeding a day.

6. The device of claim 1 wherein the structural member includes a malleable material.

7. The device of claim 1 wherein the membrane includes at least one relief feature having a triangular shape.

8. The device of claim 1 wherein the membrane includes a hook and loop fastener.

9. The device of claim 1 wherein at least one of the sensor module or the communication module is electrically shielded.

10. A system comprising:
    a wearable device having a conformable membrane, the membrane reinforced by a semi-rigid support structure, the support structure configured to retain a first portion of the membrane in a shape that conforms to a tissue surface and the membrane having an elongate second portion connected to the first portion, the elongate second portion having a relief feature configured to allow flexure in a side to side direction and the membrane including a third portion connected to the second portion, wherein the third portion includes a strap configured to at least encircle a user, the wearable device having a sensor module and a first communication module, the sensor module configured to generate an electrical signal based on a physiological parameter, the first communication module configured to wirelessly communicate data based on the electrical signal; and
    a remote device having a second communication module, the second communication module configured to wirelessly communicate the data, the remote device configured to store information based on the physiological parameter.

11. The system of claim 10 wherein the sensor module includes at least one of a pulse oximetry sensor, a regional oximetry sensor, photoplethysmography sensor, a temperature sensor, a pressure sensor, an accelerometer, a pulse rate sensor, and a cardiac output sensor, blood pressure sensor, an electrocardiography sensor, an electroencephalogram sensor, an electromyography sensor, an electrooculogram sensor, a heart rate variability sensor, an acoustic respiratory monitoring sensor, or a pulse transit timing sensor.

12. The system of claim 10 wherein the wearable device includes a display.

13. The system of claim 10 wherein the remote device includes at least one of a display, a user interface, a memory, a processor, or a network interface.

14. The system of claim 10 wherein the sensor module is coupled to the first communication module by an electrical conductor.

15. The system of claim 10 wherein the membrane includes a laminated assembly.

16. The system of claim 10 wherein the membrane includes an aperture.

17. The system of claim 16 wherein the aperture is configured to provide ventilation to an underlying tissue.

18. The system of claim 10 wherein the membrane is configured for single patient use.

19. The system of claim 10 wherein the membrane is configured to at least partially encircle a tissue.

20. A method comprising:
providing a wearable device including a pliable membrane having a structural member, the structural member configured to retain a first portion of the pliable membrane in a shape that conforms to a tissue surface, and the pliable membrane having an elongate second portion connected to the first portion, the second portion having a relief feature configured to allow flexure in a side to side direction and the membrane including a third portion connected to the second portion, wherein the third portion including a strap configured to at least encircle a user, the device including a sensor module and a communication module, the sensor module configured to generate an electrical signal based on a physiological parameter corresponding to the tissue surface, and the communication module configured to wirelessly communicate data based on the electrical signal; and
configuring a remote device to receive the data and to store the data.

21. The method of claim 20 wherein configuring the remote device includes configuring a wireless radio frequency transceiver.

22. The method of claim 20 further including affixing the wearable device to a user.

23. The method of claim 20 further including using the remote device to display the data.

* * * * *